United States Patent [19]

Sweet

[11] Patent Number: Plant 5,479

[45] Date of Patent: May 28, 1985

[54] POINSETTIA PLANT NAMED RED CHAMPION

[75] Inventor: Jack S. Sweet, St. Petersburg, Fla.

[73] Assignee: Earl J. Small Growers, Inc., Pinellas Park, Fla.

[21] Appl. No.: 515,155

[22] Filed: Jul. 19, 1983

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of poinsettia plant named Red Champion, characterized by its large and deeper than normal red bracts and darker than normal green foliage, very vigorous and strong stems, long lasting characteristics for both foliage and bracts, excellent breaking when pinched, and its ease of propagation from cuttings.

1 Drawing Figure

The present invention relates to a new and distinct cultivar of poinsettia plant known by the varietal name Red Champion, and botanically known as *Euphorbia pulcherrima.*

Red Champion resulted from a breeding program which had the objective of producing a red poinsettia having superior characteristics relative to currently available red poinsettia cultivars.

The new cultivar resulted from a cross made by applicant in Pinellas Park, Fla., with Glory, disclosed in the U.S. Plant Pat. No. 4,384, being the seed parent, and an experimental variety from Paul Ecke Poinsettias, Encinitas, Calif. and known to applicant only as R-13, being the pollen parent. The new cultivar has been asexually reproduced by applicant by cuttings taken in the greenhouses of Earl J. Small Growers, Inc., at Pinellas Park, Fla., and it has been found that the cultivar retains its distinctive characteristics through successive propagation.

The following characteristics distinguish Red Champion from its parents and some other poinsettias commercially known and used in the horticultural industry:

1. A distinctive deeper red bract color.
2. Very vigorous and strong stems to support the inflorescence.
3. The foliage is a much darker green color than other commercially grown poinsettias, and the dark green leaves are further enhanced by their deep red petioles.
4. Long lasting foliage and bracts that withstand the rigors of commercial and home use as decorative potted plants.
5. Breaks well when pinched, and very easily propagated from cuttings.

The accompanying color photographic drawing illustrates the overall appearance of a typical branched plant of the new variety, with the colors being as true as possible in color reproduction of this type.

The following is a detailed description of the new cultivar based on plants produced under commercial practices in the greenhouses of Earl J. Small Growers, Inc., Pinellas Park, Fla. The color values were taken in late spring under mid-day, natural light conditions. Color references are to the Nickerson Color Fan of the Munsell Color Company, except where general color terms of ordinary dictionary significance are used.

Red Champion has not been observed under all possible environmental conditions. The phenotype may vary significantly with variations in environment such as temperature, light intensity, and day length.

CLASSIFICATION

Botanical: *Euphorbia pulcherrima* v. Red Champion.

PARENTAGE

Female parent: Glory, U.S. Plant Pat. No. 4,384.

Male parent: An experimental variety from Paul Ecke Poinsettias, Encinitas, Calif. and known to applicant only as R-13.

PLANT

Form and growth habit: Upright and excellent branching, with strong stiff stems; breaks well when pinched, and very easily propagated from cutting.

Rooting: Cuttings root fast and produce a vigorous root system capable of supporting a strong potted plant.

Blooming season: Natural flowering season is late November to early December, with normal forcing time being approximately eight weeks. The inflorescence is very long lasting and the bracts can be expected to remain eight weeks or more on the plant.

Foliage: The leaves are alternate with a broadly oblong to broad ovate outline having deltoid acuminate apices with two or more prominent teeth at the outer ends of some lateral veins. The leaf color on the upper surface is a deep green darker than dark yellowish green 10GY-4/5. When the leaves mature the upper surface deepens in color to dark yellowish green 2.5G-4/6. The lower surface is strong yellowish green 2.5G-5/9. Leaf petioles are a destinctive dark red 5R-3/7, with the red color continuing in the midrib and fading to green about half way down the leaf.

Inflorescence:

*Bracts.*—Multiple layers of brilliant but dark red bracts which have a broadly oblong to broad ovate outline. Some bracts have deltoid accuminate apices with prominate teeth at the outer ends of some lateral veins. These large teeth appear along the entire outer edge of the leaf blade, thereby giving the same form as a broad oak leaf. The bract color on the upper side is very brilliant but darker than strong red 5R-4/12. On the under side the color is moderate red 2.5R-4/10. The bract holds its color very well for several months, and maintains its form and stiffness without drooping.

Flowers: The cyathia are grown compactly in a terminal panicle and do not spread apart as the inflorescence ages. The individual flowers are grown on strong stems and continue to develop for several months.

*Reproductive organs.*—Nectar cup: Vivid yellow 5Y-8/12. Stamens: Strong red 5R-4/12. Pollen: Vivid Yellow 2.5Y-8/12.

I claim:

1. A new and distinct cultivar of poinsettia plant named Red Champion, substantially as illustrated and described, and particularly characterized by its large and deeper than normal red bracts and darker than normal green foliage, very vigorous and strong stems, long lasting characteristics for both foliage and bracts, excellent breaking when pinched, and its ease of propagation from cuttings.

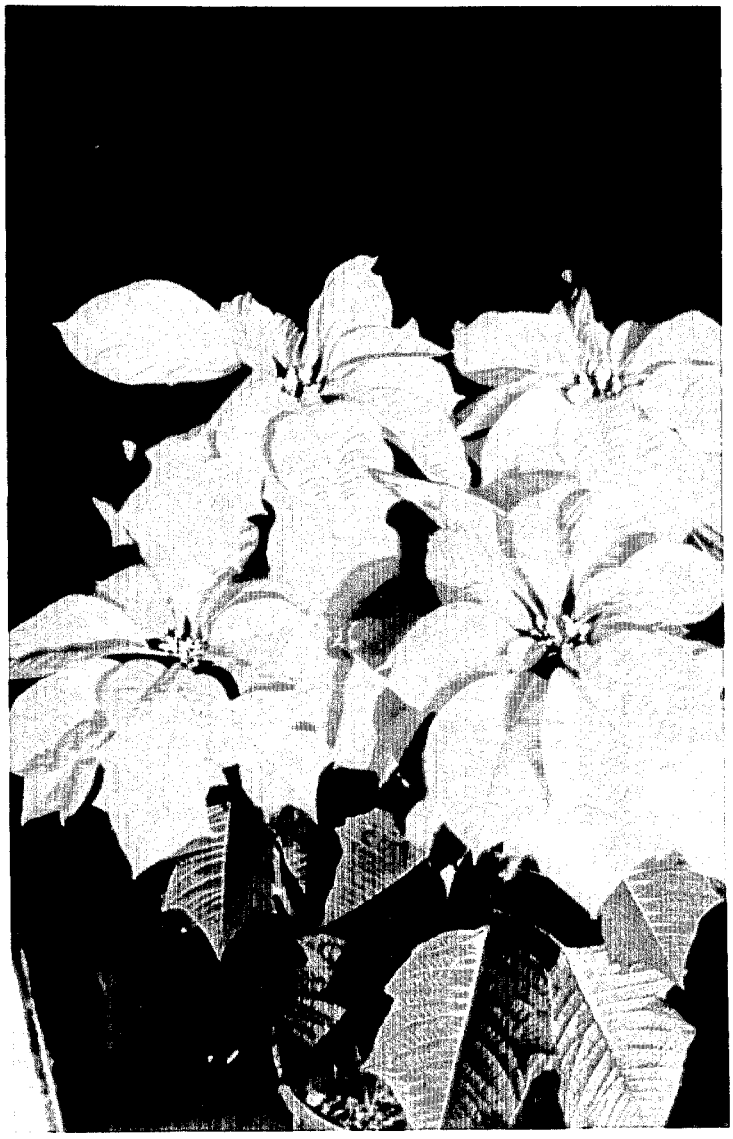

* * * * *